(12) United States Patent
Castro

(10) Patent No.: US 8,075,620 B1
(45) Date of Patent: Dec. 13, 2011

(54) DOUGHNUT-LIKE SPINAL IMPLANT

(75) Inventor: Frank Castro, Louisville, KY (US)

(73) Assignee: Cardinalspine, LLC, Louisville, KY (US)

( * ) Notice: Subject to any disclaimer, the term of this patent is extended or adjusted under 35 U.S.C. 154(b) by 399 days.

(21) Appl. No.: 12/381,955

(22) Filed: Mar. 18, 2009

(51) Int. Cl.
*A61F 2/44* (2006.01)

(52) U.S. Cl. .................. 623/17.11; 623/17.16; 606/246; 606/249

(58) Field of Classification Search .......... 606/246–249, 606/279; 623/17.11–17.16
See application file for complete search history.

(56) References Cited

U.S. PATENT DOCUMENTS

| | | | |
|---|---|---|---|
| 6,146,421 | A | 11/2000 | Gordon |
| 6,228,118 | B1 | 5/2001 | Gordon |
| 6,425,920 | B1 | 7/2002 | Hamada |
| 6,533,818 | B1 | 3/2003 | Weber et al. |
| 7,018,412 | B2 | 3/2006 | Ferreira et al. |
| 7,025,787 | B2 | 4/2006 | Bryan et al. |
| 2005/0240271 | A1 | 10/2005 | Zubok et al. |
| 2008/0045952 | A1 | 2/2008 | Kuslich |
| 2009/0036987 | A1* | 2/2009 | Oh et al. .................. 623/17.16 |

OTHER PUBLICATIONS

Barack, R. L. Revision Total Hip Arthroplasty: The Femoral Component. J. Am Acad Orthop Surg 1995; 3(2); 79-85. USA.
Castro, F. P., Jr. Stingers, Cervical Cord Neurapraxia, and Stenosis. Clin Sport Med 2003; 22: 483-492. USA.
Majd M.E., Vadhva, M. Holt, R.T. Anterior Cervical Reconstruction Using Titanium Cages With Anterior Plating. Spine 1999; 24(15): 1604-1610. USA.
Park, J.B., Cho, Y.S., Riew, K.D. Development of Adjacent-Level Ossification in Patient With an Anterior Cervical Plate. J. Bone Surg. 1005; 87-A: 558-563. USA.
Vertiflex—Print Advertisement for Octane A Spinal Implant System—Copyright 2008. USA.
Blackstone Medical Inc.—Print Advertisement for Pillar SA PEEK Spacer System—Copyright 2008. USA.
DePuy Spine Inc.—Print Advertisement for Spinal Implants—Copyright 2009. USA.
RSB Spine—Advertisement for Interplate C-P, C-PS and L-PS PEEK Spacers—Copyright 2009. USA.

* cited by examiner

*Primary Examiner* — Eduardo C Robert
*Assistant Examiner* — Christina Negrell
(74) *Attorney, Agent, or Firm* — Kenneth F. Pearce

(57) ABSTRACT

A doughnut-like lumbosacral or intervertebral implant having an asymmetrical opening surrounded by a series of load bearing sections of distinct curvatures. The doughnut-like implant can include a forwardly projecting arm and plate combination. Preferred embodiments of the doughnut-like implant can include tapered lateral annular-like sides.

27 Claims, 9 Drawing Sheets

DOUGHNUT-LIKE SPINAL IMPLANT

BACKGROUND OF THE INVENTION

1. Field of the Invention

Among other things, the present invention is related to a lumbosacral or intervertebral implant. The doughnut-like implant includes an asymmetrical opening surrounded by a series of load bearing sections of distinct curvatures. Some preferred embodiments are provided with a forwardly projecting arm and plate combination to assist with stabilization of the doughnut-like implant. Other preferred embodiments of the doughnut-like implant can include tapered lateral sections of distinct curvatures.

2. Description of the Previous Art

1) U.S. Pat. No. 6,425,920-Hamada enables a spinal fusion implant. In part, Column 38 of Hamada reads, "Continuing with a description of the implant 701, FIG. 59 is a sectional view looking toward anterior end "A". Opposite the left side 713, a right side 715 is now seen. The implant 701 has a generally toroidal extent shaped mass of bone tissue 717. The central opening 707 may be packed with a material seen as material 718 which may be one of several combinations of materials and structures. Material 718 is also shown within the slot 709."

Among other things, the '920 patent does not teach or suggest the use of an irregular central opening, an aperture located proximate the inferior edge for receiving a fastener, first and second annular-like sides distinct from the anterior and posterior curvatures, a posterior curvature protruding forward and toward the reference vertical axis, where the posterior curvature is angled more acutely than the anterior curvature, a forwardly extending arm attached to the superior edge of the anterior curvature and a plate comprising an aperture connected to the forwardly extending arm.

2) U.S. Pat. No. 6,146,421-Gordon enables a multiple axis intervertebral prosthesis. In part, Columns 3 and 4 of the '421 patent read, "The present invention relates to a variable axis intervertebral disk prosthesis (see FIG. 1). The prosthesis has two components (see FIG. 4), male 10 and female 12, and is for implantation between two adjacent vertebrae in place of a spinal disk. Attachment to the adjacent vertebrae is accomplished at least in part by means of an attachment element, preferably mechanical attachment elements such as screws 14 which pass through a flange 16. Alternatives to screws such as pegs or posts are acceptable means for attaching the components to the vertebrae, as long as they are strong enough to handle the compressive forces exerted on it, and are a reliable form of fixation. Bone cement may also be used for attachment to the adjacent vertebrae, either in place of or in addition to mechanical attachment elements. The preferred length and diameter of the mechanical attachment elements is determined by the surgeon depending on the size of the patient and the location in the spine where the disk is being replaced. If using screws, they may be inserted straight into the vertebrae or at an angle. In one preferred embodiment, the screws are inserted straight into the vertebrae (see FIG. 1). In another preferred embodiment, a screw is inserted into the vertebra at an angle (see FIG. 5).

The male portion 10 of the prosthesis comprises a cylindrical support plate 18, which in a preferred embodiment is wedge shaped. The wedge shaped plate 18 allows for building lordosis into the prosthesis. The wedge shaped plate 18 has one rough-faced surface 20 that would mate with a vertebra. In a preferred embodiment, the male component 10 is the upper component and the rough surface 20 is on the upper surface 80 of the wedge shaped plate 18 (see FIG. 4). The rough surface allows for another means of fixation to a vertebra, as an alternative to or in addition to the mechanical attachment elements. A presently preferred embodiment has both attachment elements, such as screws 14, and a rough surface 20 to provide for the most stable fixation.

Extending vertically from the edge of the upper surface 20 of the support plate is at least one flange 16. In a preferred embodiment, the male component is the upper component and the flange extends upward from the thick side of the wedge shaped plate 28 (see FIG. 1). The flange is a mounting tab that can receive the attachment elements, such as screws 14. The screws are guided through openings 22 in the flange in order to attach the male portion 10 to a vertebra. There are at least two openings 22 through which (at least two) attachment elements can pass. In a preferred embodiment, the openings 22 in the flange 16 are figure eight shaped openings 34 (see FIG. 3). The figure eight shaped opening aids in facilitating different screw heights. Different heights are chosen by the surgeon depending on what best fits each particular patient. The opening 22 can also be circular, or oval in shape."

Among other things, the '421 patent does not teach or suggest the use of doughnut-like implant with an irregular central opening, having a reference vertical axis, first and second annular-like sides distinct from the anterior and posterior curvatures, a posterior curvature protruding forward and toward the reference central vertical axis, where the posterior curvature is angled more acutely than the anterior curvature and a plate comprising an aperture, where the plate is connected with the forwardly extending arm, and where the plate extends upward from the forwardly extending arm and is generally parallel the reference axis.

3) U.S. Pat. No. 6,228,118-Gordon enables a multiple axis intervertebral prosthesis. The '118 patent has identical disclosure as the '421 patent's disclosure set forth above. Therefore, the '118 patent does not teach or suggest the use of doughnut-like implant with an irregular central opening, having a reference vertical axis, first and second annular-like sides distinct from the anterior and posterior curvatures, a posterior curvature protruding forward and toward the reference central vertical axis, where the posterior curvature is angled more acutely than the anterior curvature and a plate comprising an aperture, where the plate is connected with the forwardly extending arm, and where the plate extends upward from the forwardly extending arm and is generally parallel the reference axis.

4) U.S. Pat. No. 6,533,818-Weber, et al. enables an artificial spinal disc. In part, Column 4 of the '818 patent reads, "FIG. 1 shows a perspective view of one embodiment of the artificial spinal disc implant. The implant 10 is designed to approximate the shape and size of natural intervertebral discs. It has a planar top 12 and bottom 14 that bond to the vertebral bone when implanted in the vertebral spine. The implant is comprised of three distinct layers including a central layer 16."

Among other things, the '818 patent does not teach or suggest the use of doughnut-like implant with an irregular central opening, having a reference vertical axis, a posterior curvature protruding forward and toward the reference vertical axis, where the posterior curvature is angled more acutely than the anterior curvature, a first annular-like side distinct from the anterior and posterior curvatures and connected with the anterior solid curvature and the posterior curvature, where the first annular-like side includes an upper boundary and a lower boundary, and where the upper boundary and the lower boundary taper toward each other as the first annular-like side traverses from the anterior curvature to the posterior curvature, a second annular-like side distinct from the anterior and posterior curvatures and connected with the anterior curvature and the posterior curvature, where the second annular-like side includes an upper boundary and a lower boundary, and where the upper boundary and the lower boundary taper toward each other as the second annular-like side traverses from the anterior curvature to the posterior curvature, a forwardly extending arm attached to the superior edge of the anterior curvature, and a plate comprising an aperture, where the plate is connected with the forwardly extending arm, and where the plate extends upward from the forwardly extending arm and is generally parallel the reference axis.

5) U.S. Pat. No. 7,018,412-Ferreira, et al. enables an allograft spinal implant. In part, Column 5 of the '412 patent reads, "With reference to FIG. 5, a simplified lateral side view of an allograft spinal implant constructed according to the teachings of a second preferred embodiment of the present invention is generally identified at reference numeral 30. As with the first preferred embodiment, the implant is particularly intended for cervical spine applications. The implant 30 of the second preferred embodiment will be understood to be identical to the spinal implant 10 of the first preferred embodiment with the exception that superior and inferior end faces 32 and 34 of the implant 30 are not parallel to one another but relatively angled to accommodate natural spinal lordosis. In one exemplary application, the superior and inferior end faces 32 and 34 are angled from one another at approximately 5°. However, it is anticipated that the lordodic angle may fall within the range of 0° to approximately 10° or greater.

The implant 30 includes an anterior height h 1, a posterior height h 2, an outer diameter or depth D, and a through hole 36 having a diameter d. As with the spinal implant 10 of the first preferred embodiment, the through hole diameter d of the implant 30 preferably ranges from 0 mm to approximately 6 mm and the overall diameter or depth D preferably ranges from approximately 8 mm to approximately 15 mm. In these applications, the anterior height preferably ranges from approximately 8 mm to approximately 14 mm and the posterior height ranges from approximately 5 mm to approximately 11 mm."

In part, Column 5 of the '412 patent reads, "With reference to FIGS. 25-28, various stages of the implant 180 during a manufacturing process are illustrated. As shown in FIG. 25, a rough implant 121 is harvested from a transverse section of cortical bone. The rough implant 121 includes a through hole 122 that is naturally formed in the bone by the intramedullary canal."

In part, Column 8 of the '412 patent reads, "With to FIGS. 45-48, an allograft spinal implant constructed in accordance with the teachings of a twelfth preferred embodiment of the present invention is illustrated and generally identified at reference character 250. The implant 250 is particularly intended for anterior lumbar interbody fusion applications. The long axis of the donor bone is indicated by arrow C. The implant 250 defines a generally central aperture 252. As with various prior embodiments of the present invention, the implant 250 is formed to include a plurality of concentric-arc ridges 254 on both the inferior and superior surfaces. In the embodiment illustrated, the superior and inferior end faces are angled from one another at approximately 6°. However, it is anticipated that the lordodic angle may fall within the range of 0° to approximately 6° or greater than 6°."

Among other things, the '412 patent does not teach or suggest the use of a biocompatible metallic or plastic doughnut-like implant, a forwardly extending arm attached to the superior edge of the anterior curvature and a plate comprising an aperture, where the plate is connected with the forwardly extending arm, and where the plate extends upward from the forwardly extending arm and is generally parallel the reference axis.

6) U.S. Pat. No. 7,025,787-Bryan, et al. enables an implantable joint prosthesis and associated instrumentation. In part, Columns 11 and 12 of the '787 patent read, "Preferably, shells 20, 40 are cup-like so as to include an outer convex surface 23 and an inner concave surface 21, 41. The outer surfaces 23 can be coated with a nonspherical sintered bead coating 22, 42, or with some other coating that will promote bony ingrowth. The inner surfaces 21, 41 (shown in FIG. 6) are preferably very smooth, and may be machined or polished.

The shells 20, 40 include a number of geometric features that as described in further detail below cooperate with other components of the devices. Specifically, these features include a central retaining post 27, 47, an outer circumferential groove 82, 84, and a radial stop or an extension 86, 88. The central retaining post 27, 47 extends axially from inner surfaces 21, 41. In addition, each shell 20, 40 includes an edge 73, 74, respectively. The outer circumferential grooves 82, 84 extend into the edges 73, 74 of the shells 20, 40. As seen best in FIG. 6, the radial stops or extensions 86, 88 extend from the edges 73, 74 in a direction generally perpendicular to the general plane of the shells 20, 40.

Each shell 20, 40 may also be provided with tabs or flanges 25, 45. The tabs or flanges 25, 45 extend from a portion of the edges 73, 74 in a direction generally perpendicular to the general plane of the shells 20, 40, but in a direction generally opposite the radial stops or extensions 86, 88. The tabs or flanges 25, 45 help to prevent long-term migration within the disc space, as well as catastrophic posterior expulsion, and the resulting damage to the spinal cord, other nerves, or vascular structures. The tabs or flanges 25, 45 may contain openings 26, 46 that can releasably engage an insertion tool (not shown). The insertion tool will generally contain flexible prongs to releasably engage openings 26, 46. The insertion tool will also generally include a disengagement block that can press against the side of the implant once it has been properly positioned in the intervertebral space and force the openings 26, 46 off of the prongs of the tool.

The shells 20, 40 can be made from any suitable biocompatible rigid material. In accordance with a preferred embodiment, the shells 20, 40 are made from a titanium alloy, and most preferably the titanium alloy is ASTM F-136. The bead coating 22, 42, however, is preferably made from ASTM F-67 pure titanium.

As shown best in FIG. 7, central body 60 is preferably a donut-shaped structure, and includes a convex upper contact surface 94, a convex lower contact surface 96, and a central axial opening 98 formed through an inner surface 67 of the central body. In addition, central body member 60 preferably includes an upper shoulder 92 and a lower shoulder 90. Each shoulder 90, 92 consists of an indentation in the surface of the central body member which defines a ledge that extends around the circumference of the central body 60."

Among other things, the '787 patent does not teach or suggest the use of doughnut-like implant with an irregular central opening, having a reference central vertical axis, an anterior curvature comprising an aperture located proximate the inferior edge for receiving a fastener, a posterior curvature protruding forward and toward the reference central vertical axis, where the posterior curvature is angled more acutely than the anterior curvature, a first annular-like side distinct from the anterior and posterior curvatures and connected with the anterior solid curvature and the posterior curvature, where the first annular-like side includes an upper boundary and a lower boundary, and where the upper boundary and the lower boundary taper toward each other as the first annular-like side traverses from the anterior curvature to the posterior curvature, a second annular-like side distinct from the anterior and posterior curvatures and connected with the anterior curvature and the posterior curvature, where the second annular-like side includes an upper boundary and a lower boundary, and where the upper boundary and the lower boundary taper toward each other as the second annular-like side traverses from the anterior curvature to the posterior curvature and a plate comprising an aperture, where the plate is connected with the forwardly extending arm, and where the plate extends upward from the forwardly extending arm and is generally parallel the reference axis.

7) US Pub. Patent App. No. 20050240271-Zubok, et al. discloses a cervical disc replacement. Paragraphs 44-46 of Zubok read, "Referring now to FIGS. 1-5, an artificial disc implant 100 of the present invention is shown in perspective, anterior, lateral, lateral cutaway, and posterior cutaway views, respectively. The implant 100 includes a first (e.g., upper) element 200 and a second (e.g., lower) element 300, each having an outwardly facing vertebral body contact surface 202, 302, and each having an inwardly facing articulation surface 204, 304. The elements 200, 300 are disposed as shown with the articulation surfaces 204, 304 nested against one another, and the vertebral body contact surfaces 202, 302 facing away from one another. When the implant 100 is disposed in an intervertebral disc space in a cervical spine, in this configuration and with the vertebral body contact surfaces 202, 302 engaged with respective adjacent vertebral body endplates (not shown), the implant 100 enables the adjacent vertebral bones to move relative to one another in accordance with proper anatomical motion, as further described below.

Preferably, at least one (and more preferably both) of the elements 200, 300 has at least one long-term fixation structure (e.g., flange 206, 306) having at least one feature (e.g., through hole 208 a, 208 b, 308) for securing the element to an adjacent vertebral body. For example, the upper element 200 has an anterior flange 206 that extends upwardly and has two through holes 208 a, 208 b, each of which accepts a bone screw (not shown). And, for example, the lower element 300 has an anterior flange 306 that extends downwardly and has one through hole 308 that accepts a bone screw (not shown). Once the elements 200, 300 are disposed in the intervertebral space with the vertebral body contact surfaces 202, 302 engaged with respective adjacent vertebral body endplates (not shown), securing of bone screws through the holes 208 a, 208 b, 308 and into the anterior surfaces of the adjacent vertebral bones helps prevent the elements from becoming dislodged from, or displaced in, the intervertebral space. Preferably, the bore axes of the through holes 208 a, 208 b, 308 are angled toward the adjacent vertebral body as shown.

Further preferably, at least one (and more preferably both) of the elements 200, 300 has at least one short-term fixation structure (e.g., spike 210 a, 210 b, 310 a, 310 b) for securing the element to an adjacent vertebral body (and more preferably to an adjacent vertebral body endplate). For example, each of the elements 200, 300 has a respective pair of outwardly directed spikes 210 a, 210 b, 310 a, 310 b. Once the elements 200, 300 are disposed in the intervertebral space with the vertebral body contact surfaces 202, 302 engaged with respective adjacent vertebral body endplates (not shown), the spikes 210 a, 210 b, 310 a, 310 b dig into the adjacent vertebral body endplates under the compression along the longitudinal axis of the spinal column, and thus help prevent the elements from becoming dislodged from, or displaced in, the intervertebral space. Preferably, each of the spikes 210 a, 210 b, 310 a, 310 b is sloped toward the vertebral body contact surface 202, 302 and toward the posterior direction on its posterior side as shown, to facilitate ease of insertion of the implant 100 into the intervertebral space, and is either perpendicular to the vertebral body contact surface 202, 302 on its anterior side (as shown) or sloped toward the vertebral body contact surface 202, 302 and toward the posterior direction on its anterior side (not shown), to help prevent the elements 200, 300 from anteriorly (or otherwise) slipping out of the intervertebral space."

Among other things, the '271 application does not teach or suggest the use of doughnut-like implant with an irregular central opening, having a reference vertical axis, a posterior curvature protruding forward and toward the reference vertical axis, where the posterior curvature is angled more acutely than the anterior curvature, a first annular-like side distinct from the anterior and posterior curvatures and connected with the anterior solid curvature and the posterior curvature, where the first annular-like side includes an upper boundary and a lower boundary, and where the upper boundary and the lower boundary taper toward each other as the first annular-like side traverses from the anterior curvature to the posterior curvature, a second annular-like side distinct from the anterior and posterior curvatures and connected with the anterior curvature and the posterior curvature, where the second annular-like side includes an upper boundary and a lower boundary, and where the upper boundary and the lower boundary taper toward each other as the second annular-like side traverses from the anterior curvature to the posterior curvature and a plate comprising an aperture, where the plate is connected with the forwardly extending arm, and where the plate extends upward from the forwardly extending arm and is generally parallel the reference axis.

8) US Pub. Patent App. No. 20080045952-Kuslich discloses an annulus-reinforcing band. Paragraph 96 of Kuslich reads, "The band 12 is pliable and malleable before its interior space 14 (not shown in FIG. 2) is filled with the contents to be described. While in this initial condition, the band 12 may be passed, in a collapsed state, through a relatively small tube or portal, such as recited in U.S. Pat. Nos. 5,571,189 and 5,549,679, the entire contents of both references being incorporated herein by reference. This feature is important because access to the intervertebral disc is limited by anatomy and therefore safety considerations direct us to use the smallest possible portal of entry."

Among other things, the '952 application does not teach or suggest the use of doughnut-like implant with an irregular central opening, having a reference vertical axis, a posterior curvature protruding forward and toward the reference vertical axis, where the posterior curvature is angled more acutely than the anterior curvature, a first annular-like side distinct from the anterior and posterior curvatures and connected with the anterior solid curvature and the posterior curvature, where the first annular-like side includes an upper boundary and a lower boundary, and where the upper boundary and the lower boundary taper toward each other as the first annular-like side traverses from the anterior curvature to the posterior curvature, a second annular-like side distinct from the anterior and posterior curvatures and connected with the anterior curvature and the posterior curvature, where the second annular-like side includes an upper boundary and a lower boundary, and where the upper boundary and the lower boundary taper toward each other as the second annular-like side traverses from the anterior curvature to the posterior curvature, a forwardly extending arm attached to the superior edge of the anterior curvature, and a plate comprising an aperture, where the plate is connected with the forwardly extending arm, and where the plate extends upward from the forwardly extending arm and is generally parallel the reference axis.

SUMMARY OF THE INVENTION

Unlike traditional spinal implants, the present invention provides is a doughnut-like spinal implant that is particularly well suited for implantation into the patient's lumbosacral region. The current doughnut-like spinal implant has an asymmetrical opening that can be filled with osteogenic substances. Load bearing annular-like sections of the current implant engage vertebra and resist spinal compression and gravitational forces.

An aspect of the present invention is to provide an embodiment of a doughnut-like implant that is particularly well suited for implantation into the patient's lumbosacral region.

Still another aspect of the present invention is to provide an embodiment of a doughnut-like implant that is manufactured of biocompatible metals, plastics or combinations thereof.

It is another aspect of the present invention to provide an embodiment of a doughnut-like implant that has distinct load bearing sections of separate curvatures.

Yet another aspect of the present invention is to provide an embodiment of a doughnut-like implant that has tapered sides.

Still another aspect of the present invention is to provide an embodiment of a doughnut-like implant that has a forwardly projecting arm.

It is still another aspect of the present invention to provide an embodiment of a doughnut-like implant that has a forwardly projecting arm and a plate extending upwardly therefrom.

Yet still another aspect of the present invention is to provide an embodiment of an integral doughnut-like implant that has distinct load bearing sections of separate curvatures.

It is still another aspect of the present invention to provide an embodiment of a doughnut-like implant that has a protruding anterior curvature and a protruding posterior curvature.

Still another aspect of the present invention is to provide an embodiment of a doughnut-like implant where the anterior curvature is angled more acutely than the posterior curvature.

It is another aspect of the present invention to provide an embodiment of a doughnut-like implant that has a forwardly protruding anterior curvature and a forwardly posterior curvature.

Yet still another aspect of the present invention is to provide embodiment of a doughnut-like implant that has roughened upper and lower edges.

It is still another aspect of the present invention to provide an embodiment of a doughnut-like implant that a porous coating applied to at least part of the implant's upper or lower edges.

Still another aspect of the present invention is to provide an embodiment of a doughnut-like implant that has one or more windows.

Yet still another aspect of the present invention is to provide one or more covers for the doughnut-like implant's windows.

An embodiment of the present invention can be described as a biocompatible metallic, plastic or combined metallic-plastic doughnut-like implant capable of frontal insertion between a superior and inferior lumbosacral vertebra; said doughnut-like implant comprising: a) an asymmetrical central opening having a central vertical axis; b) an anterior curvature protruding forward and away from the central vertical axis, wherein the anterior curvature has superior and inferior edges; the anterior curvature further comprising one or more apertures located proximate the inferior edge for receiving'one or more fasteners; c) a posterior curvature protruding forward and toward the central vertical axis, wherein the posterior curvature has superior and inferior edges, and wherein the posterior curvature is angled more acutely than the anterior curvature; d) a first annular-like side distinct from the anterior and posterior curvatures and connected with the anterior curvature and the posterior curvature, wherein the first annular like side includes an upper boundary and a lower boundary, and wherein the upper boundary and the lower boundary taper toward each other as the first annular-like side traverses from the anterior curvature to the posterior curvature; e) a second annular-like side distinct from the anterior and posterior curvatures and connected with the anterior curvature and the posterior curvature, wherein the second annular-like side includes an upper boundary and a lower boundary, and wherein the upper boundary and the lower boundary taper toward each other as said second annular-like side traverses from said anterior curvature to said posterior curvature; f) a forwardly extending arm attached to the superior edge of the anterior curvature; and g) a plate comprising an aperture, wherein the plate is connected with the forwardly extending arm, wherein the plate extends upward from the forwardly extending arm, wherein the plate is generally parallel a reference plane intersecting the first annular-like side and the second annular-like side.

Another embodiment of the present invention can be described a biocompatible metallic, plastic or combined metallic-plastic doughnut-like implant capable of frontal insertion between a superior and inferior lumbosacral vertebra, wherein the doughnut-like implant comprises a plurality of distinct generally upright load supporting curvatures; the doughnut-like implant further comprising: a) an asymmetrical central opening, including a central vertical axis, surrounded by the plurality of distinct generally upright load supporting curvatures; b) an anterior member, of said plurality of distinct generally upright load supporting curvatures, protruding forward and away from said central vertical axis; the anterior member further comprising one or more apertures proximate an inferior edge of the anterior member; c) a posterior member, of said plurality of distinct generally upright load supporting curvatures, protruding forward and toward the central vertical axis; the posterior member angled more acutely than the anterior member; d) a first tapered lateral member, of the plurality of distinct generally upright load supporting curvatures, intermediate between and connected with the anterior and the posterior members; said first tapered lateral member comprising an upper boundary and a lower boundary that taper toward each other; e) a second tapered lateral member, of the plurality of distinct generally upright load supporting curvatures, intermediate between and connected with the anterior and the posterior members; the second tapered lateral member comprising an upper boundary and a lower boundary that taper toward each other; f) a forwardly extending arm attached proximate an upper edge of the anterior member; and g) a plate, comprising an aperture, connected with the forwardly extending arm.

Yet another embodiment of the present invention can be described as a biocompatible doughnut-like implant capable of frontal insertion between a superior and an inferior vertebra; said doughnut-like implant comprising: a) an asymmetrical opening comprising a reference generally vertical axis; b) distinct load bearing curvatures surrounding said asymmetrical opening; the distinct load bearing curvatures comprising superior and inferior edges; c) a porous coating applied to one or more of the superior or inferior edges; d) a first load bearing curvature, of the load bearing curvatures, protruding forward and away from the reference axis; said first load bearing curvature further comprising one or more apertures; e) a second load bearing curvature, of said load bearing curvatures, protruding toward the reference axis, wherein the second load bearing curvature is angled more acutely than the first load bearing curvature; third and fourth load bearing curvatures, intermediate between and connected with the first load bearing curvature and the second load bearing curvature; and g) a reference plane bisecting the third and fourth load bearing curvatures.

In still another embodiment, the present invention can be described as a biocompatible doughnut-like implant capable of frontal insertion between a superior and an inferior vertebra; the doughnut-like implant comprising an opening enclosed by a series of interconnected load bearing generally upright sections, wherein adjacent sections of the interconnected load bearing generally upright sections include distinct curvatures, and wherein the series further comprises: a) an anterior section protruding forwardly and comprising one or more apertures; b) a posterior section protruding forwardly and angled more acutely than the anterior section; c) first and second opposed lateral sections intermediate between and connected with the forward and the rearward sections; and d) a reference plane bisecting the first and the second opposed lateral sections.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

In the most general sense, the present invention is an implant that can be inserted into a cavity of the spinal column. Surgical removal of a part of the spine creates the cavity that can receive the implant. The doughnut-like implant includes an asymmetrical opening surrounded by distinct load bearing sections that resist the compression associated with gravitational forces on the spinal column. Load bearing sections can be manufactured of biocompatible metals, plastics or combinations thereof, and preferred embodiments of the doughnut-like implant are manufactured of titanium, titanium alloys, stainless steel, non-resorbable and resorbable polymers. In the practice of select embodiments of the present invention, during surgical procedures, osteogenic substances are placed into the asymmetrical opening. Select preferred embodiments of the current doughnut-like implant can be provided with an arm and plate combination that can assist in further stabilizing the implant against spinal compression and gravitational forces. Other select preferred embodiments can also include an anterior window. Still other select preferred embodiments are provided with a cover for the anterior window. Yet still other select preferred embodiments are provided with porous coating.

The present doughnut-like implant is well suited for implantation though the patient's frontal side. And it has been discovered that the doughnut-like implant is particularly well suited for insertion into the patient's lumbosacral region. Thus, the current doughnut-like implant meets the long felt but unfilled need of providing a unique load bearing implant tailored for the patient's lumbosacral region that can be inserted through a frontal surgically created field anterior to the patient's lumbosacral region.

Figure 1:
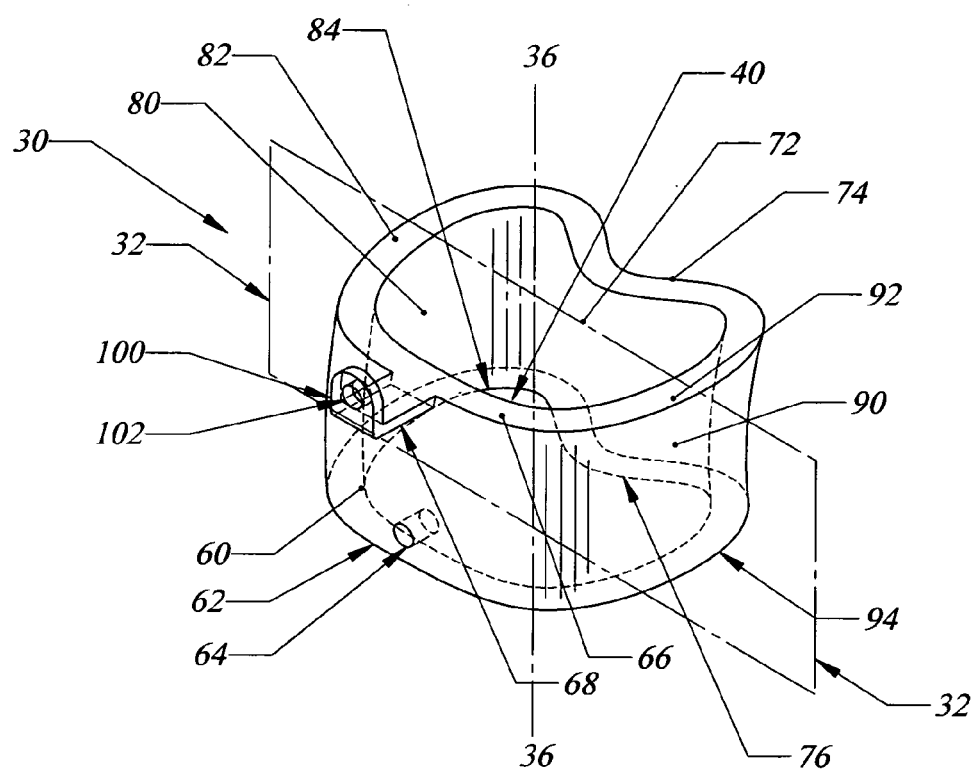
FIG. 1 is a frontal perspective of an embodiment of the doughnut-like implant.

FIG. 1 is a frontal perspective of doughnut-like implant (30) that has a central vertical reference plane (32) that is coplanar with reference central vertical axis (36-36). Asymmetrical opening (40) is surrounded by a series of load bearing curved sections.

Anterior curvature (60) protrudes forward and away from central vertical reference axis (36-36). Proximate the center of lower edge (62) of anterior curvature (60) is aperture (64). Extending forwardly from about an upper edge (66) of anterior curvature (60) is arm (68) supporting plate (100) that includes aperture (102). Fasteners (not shown in this view), such as screws, can be inserted through apertures (64) and (102) to assist in securing doughnut-like implant (30) to vertebra.

Posterior curvature (72) protrudes forward toward central vertical reference axis (36-36). Preferred embodiments of doughnut-like implant (30) have posterior curvature (72) that is angled more acutely than anterior curvature (60). Curvature (72) is acutely angled to prevent doughnut-like implant (30) from impinging on the spinal cord (not shown in this view) after doughnut-like implant (30) is insert between superior and inferior vertebra (not shown in this view). Posterior curvature (72) has upper edge (74) and lower edge (76).

Lateral curvature or annular-like side (80) of doughnut-like implant (30) is intermediate between anterior curvature (60) and posterior curvature (72). Lateral curvature (80) has upper boundary or edge (82) and lower boundary or edge (84). Annular-like side (80) is angled outwardly and away from central reference vertical axis (36).

Lateral curvature or annular-like side (90) of doughnut-like implant (30) is opposite annular-like side (80) of doughnut-like implant (30). Lateral section (90) is intermediate between anterior curvature (60) and posterior curvature (72). Lateral curvature (90) has upper boundary or edge (92) and lower boundary or edge (94). Annular-like side (90) is angled outwardly and away from central reference vertical axis (36-36).

Figure 1A:
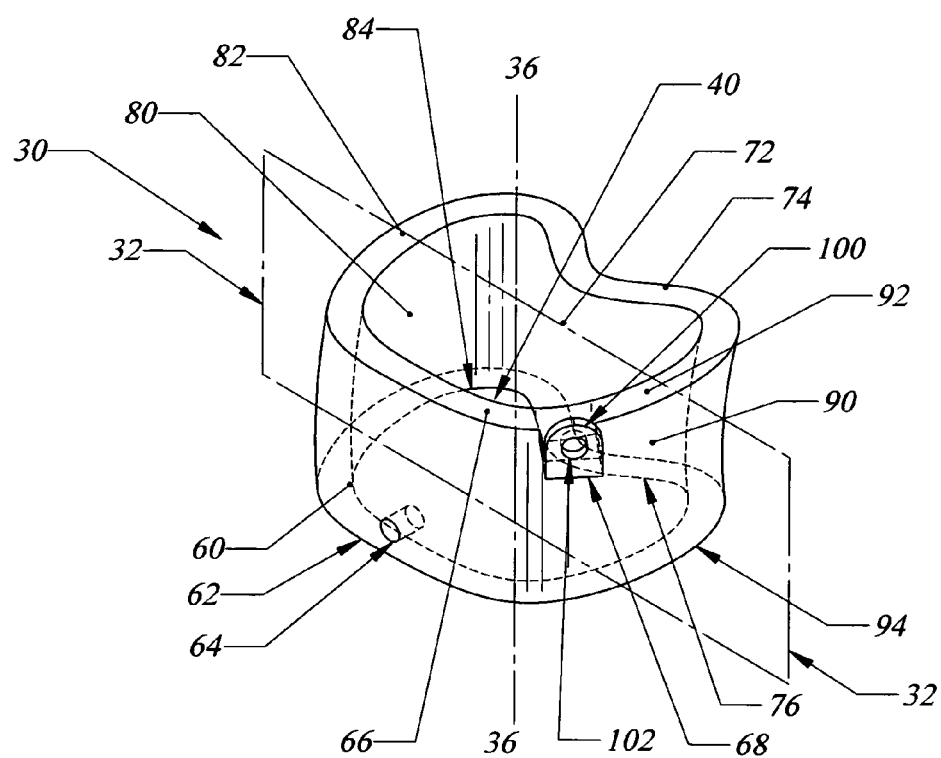
FIG. 1A is a frontal perspective of an embodiment of the doughnut-like implant.

As shown in FIG. 1, central reference plane (32-32) intersects or bisects annular-like sides (80 and 90). In select preferred embodiments, plate (100) is generally parallel reference plane (32). In other preferred embodiments, doughnut-like implant (30) does not include arm (68) or plate (100). FIG. 1A is a frontal perspective of another embodiment of doughnut-like implant (30) where arm (68) and plate (100) are offset laterally from aperture (64).

Figure 2:
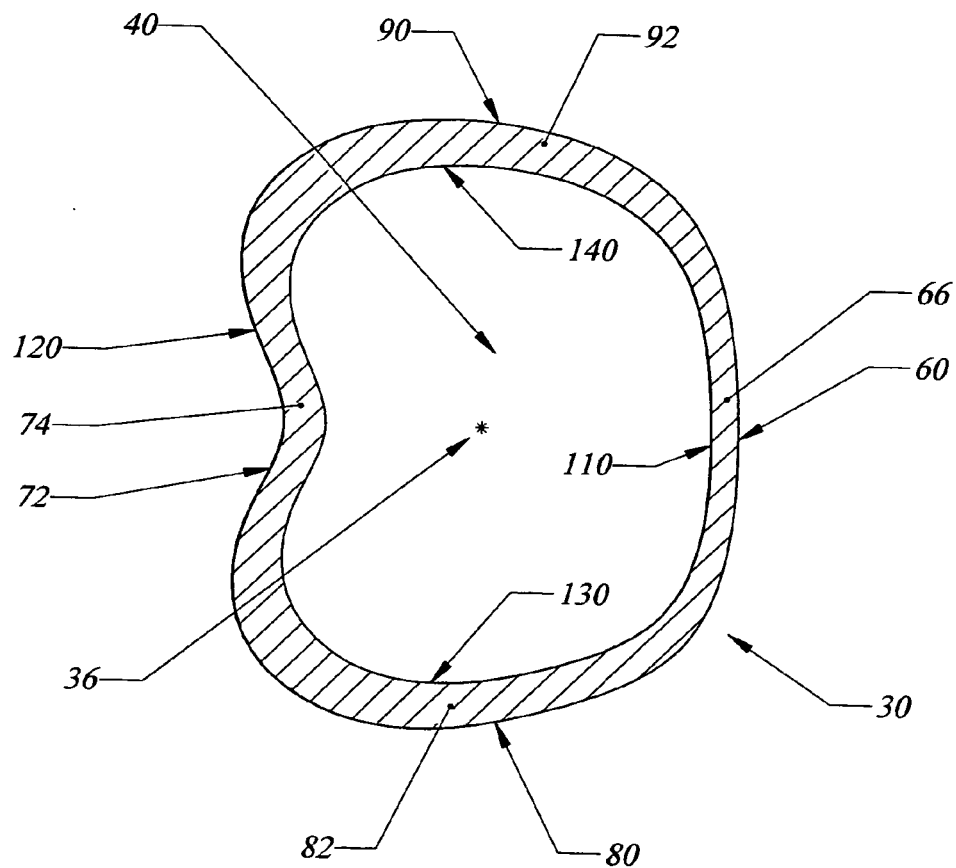
FIGS. 2 and 2A are top plan views of embodiments of doughnut-like implant.
Figure 2A:
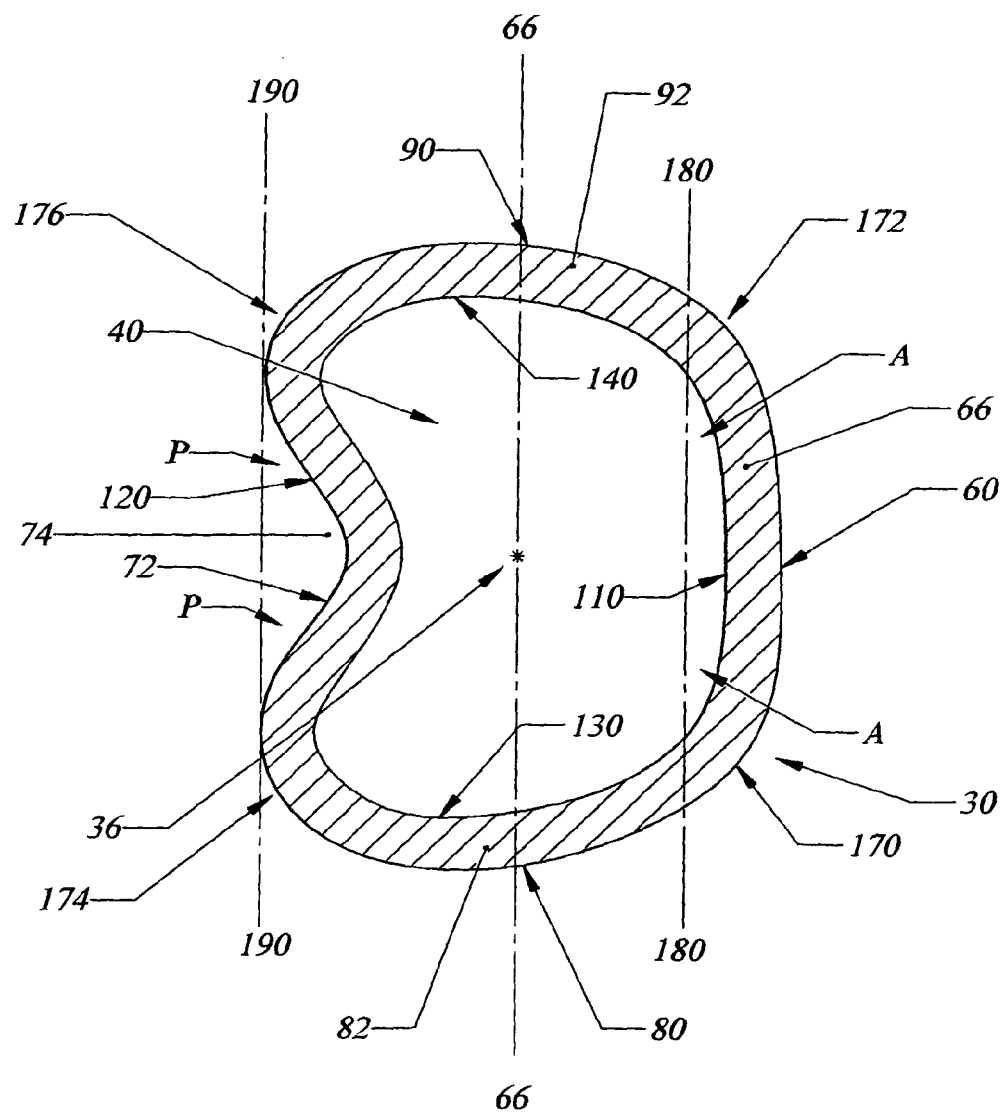

FIGS. 2 and 2A are top plan views of doughnut-like implant (30). Asymmetrical opening (40) is surrounded by anterior section (60), posterior section (72) and lateral sections (80 and 90). Upper edges (66, 74, 82 and 92) of sections (60, 72, 80 and 90) are shown in FIG. 2. Section (60) has curvature (110). Section (72) is provided with curvature (120). And sections (80 and 90) have curvatures (130 and 140), respectively. Each curvature (110, 120, 130 and 140) is distinct from its adjacent curvature (110, 120, 130 and 140).

In preferred embodiments of the present invention, curvature (120) of posterior section (72) is angled to protrude more acutely toward central vertical reference axis (36-36) than curvature (110) of anterior section (60) is angled to protrude away from reference axis (36-36). Posterior section (72) is angled to prevent doughnut-like implant (30) from impinging on the spinal cord (not shown in this view). Depending on engineering parameters, curvatures (130 and 140) of lateral sections (80 and 90) are similar or identical.

As used herein, anterior vertical reference plane (180-180) extends between intersection (170) of curvature (130) and curvature (110) and intersection (172) of curvature (140) and curvature (110). An anterior protrusion angle (A) is measured from the intersection of anterior vertical reference plane (180-180) and curvature (110). Preferred embodiments of the current invention practice doughnut-like implants (30) with anterior protrusion angles (A) of about 30 degrees or less.

As used herein, posterior vertical reference plane (190-190) extends between intersection (174) of curvature (130) and curvature (120) and intersection (176) of curvature (140) and curvature (120). A posterior protrusion angle (P) is measured from the intersection of anterior vertical reference plane (190-190) and curvature (120). Preferred embodiments of the current invention practice doughnut-like implants (30) with posterior protrusion angles (P) of more than 30 degrees. Depending on predetermined engineering parameters, anterior vertical reference plane (180-180) and posterior vertical reference plane (190-190) can be parallel each other or with central vertical reference plane (32-32).

Figure 3:
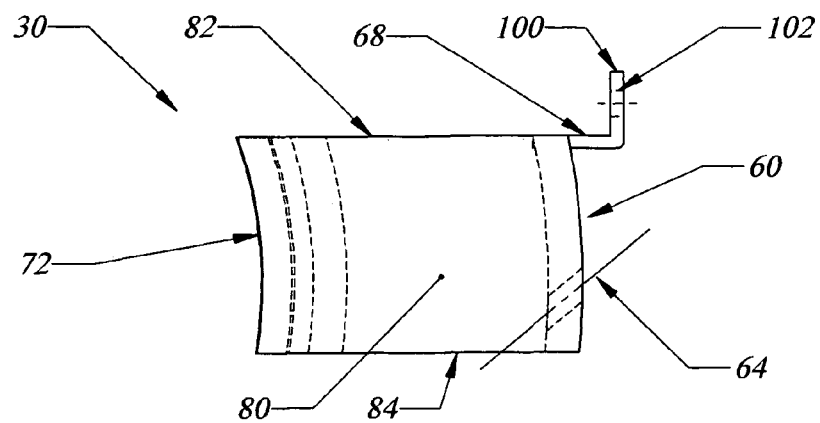
FIG. 3 is a lateral representation of an embodiment of doughnut-like implant.
Figure 3A:
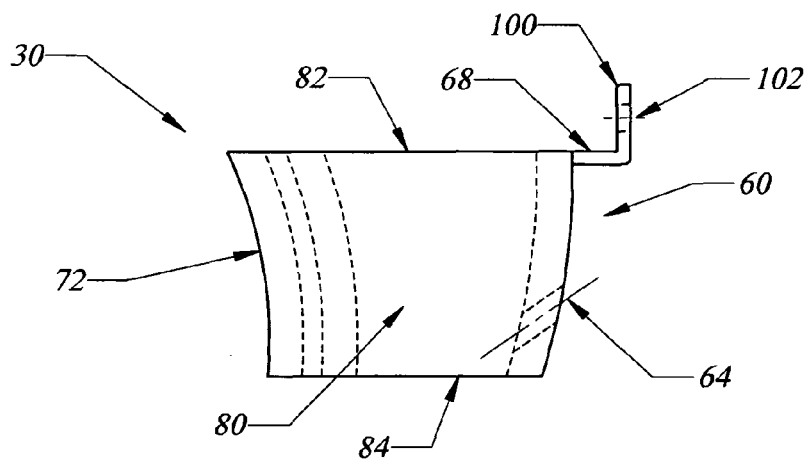
FIG. 3A is a lateral representation of an embodiment of doughnut-like implant.

With the view centered on the outward side of annular-like side (80), FIG. 3 is a lateral representation of an embodiment of doughnut-like implant (30). Aperture (64) (shown in phantom) is angled downward. Arm (68) extends forwardly from anterior curved section (60) of doughnut-like spinal implant (30). In the accordance with the present invention arm (68) can extend forwardly up to about 10 millimeters, and preferably, 5 millimeters or less. Extending upwardly from arm (68) is plate (100) having aperture (102) for receiving a fastener (not shown in this view). Upper edge (82) and lower edge (84) of annular-like side (80) follow the same arc. FIG. 3A is a lateral representation of doughnut-like implant (30) where arc of edge (82) of doughnut-like implant (30) encompasses a greater area than arc of edge (84) of doughnut-like implant (30). In the embodiment portrayed in FIG. 3A, anterior section (60), posterior section (72) and lateral sections (80 and 90) are tapered between edges (82 and 84) of doughnut-like implant (30).

Figure 4:
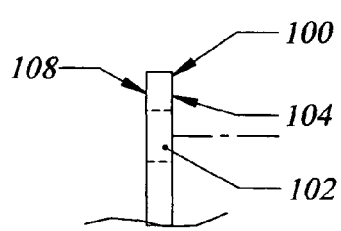
FIG. 4 is a lateral view of an embodiment of a plate of the current invention.

FIG. 4 is a lateral view of an embodiment of plate (100). Aperture (102), shown in phantom, is generally perpendicular to outward side (104) and inward side (108) of plate (100).

Figure 5:
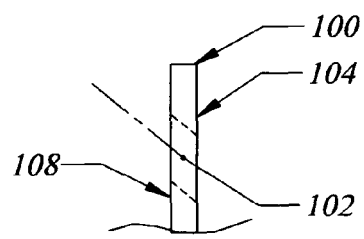
FIG. 5 is a lateral view of another embodiment of a plate of the present invention.

FIG. 5 is a lateral view of another embodiment of plate (100). Aperture (102), shown in phantom, is angled upward as aperture (102) traverses from the outward side (104) through inward side (108) of plate (100).

Among other things, along with easier insertion of a fastener into aperture (102), utilization of the arm (68) and plate (100) embodiments of the current invention allows for easier placement and tightening of the superior fasteners, i.e., specialized screwdrivers for use about the pelvic area can be eliminated. The angling of apertures (102) and (64) enhances the load bearing capacity of doughnut-like implants (30) as well reducing the likelihood that screws will back out of the vertebra as the spinal column is subjected to movement and gravitational forces. Further, the angling of apertures (102) and (64) allows for fasteners of greater length which also improves the stability of the doughnut-like implant (30).

Figure 6:
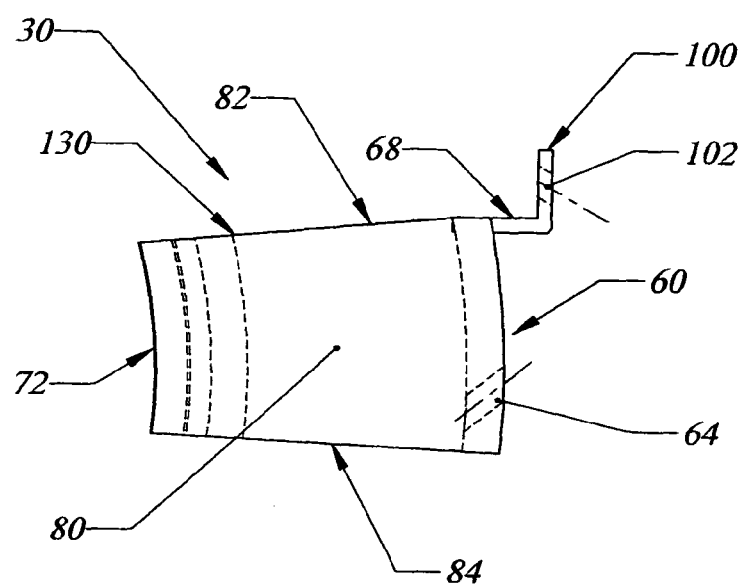
FIG. 6 is a lateral representation of an embodiment of the doughnut-like implant.

With the view centered on the outward side of annular-like side (80), FIG. 6 is a lateral representation of an embodiment of doughnut-like implant (30). Aperture (64) (shown in phantom) is angled downward. Arm (68) extends forwardly from anterior curved section (60) of doughnut-like spinal implant (30). Extending upwardly from arm (68) is plate (100) having aperture (102) for receiving a fastener (not shown in this view). Upper edge (82) and lower edge (84) of curvature (80) are tapered. In select preferred embodiments, upper boundary (82) and lower boundary of annular-like side (80) taper toward each other as curvature (130) traverses from anterior curved section (60) to posterior curved section (72).

Figure 7:
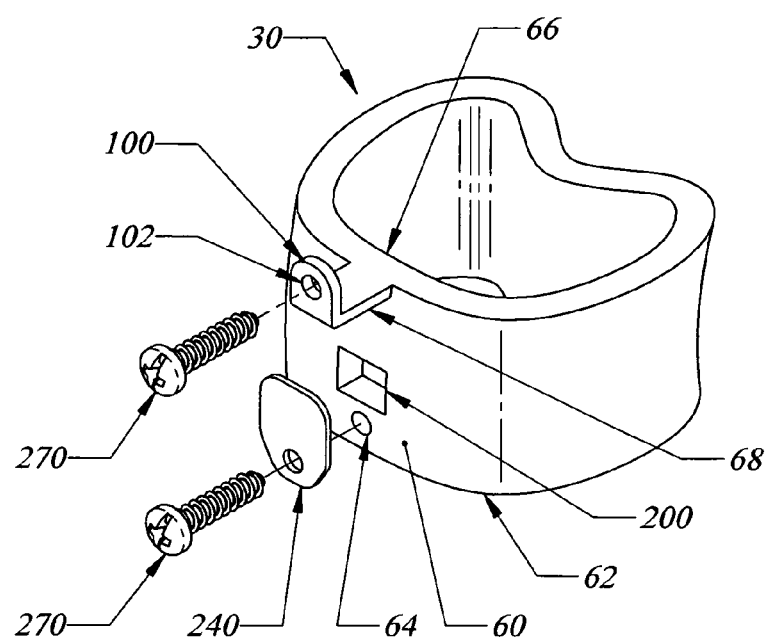
FIG. 7 is an exploded perspective of an anterior curved section of an embodiment of the doughnut-like implant.

FIG. 7 is an exploded perspective of another embodiment of doughnut-like implant (30). Anterior curved section (60) has lower edge (62), upper edge (66) and arm (68) extending forwardly from anterior curved section (60). Attached to arm (68) is plate (100) that includes aperture (102) for receiving fastener (270). Anterior curved section (60) includes window (200) and aperture (64) proximate to window (200). Window (200) allows addition of osteogenic substances into the doughnut-like implant after the implant has been inserted between two vertebras. Along with securing doughnut-like implant (30) to bone, fastener (270) also secures cover (240) about window (200).

Figure 8:
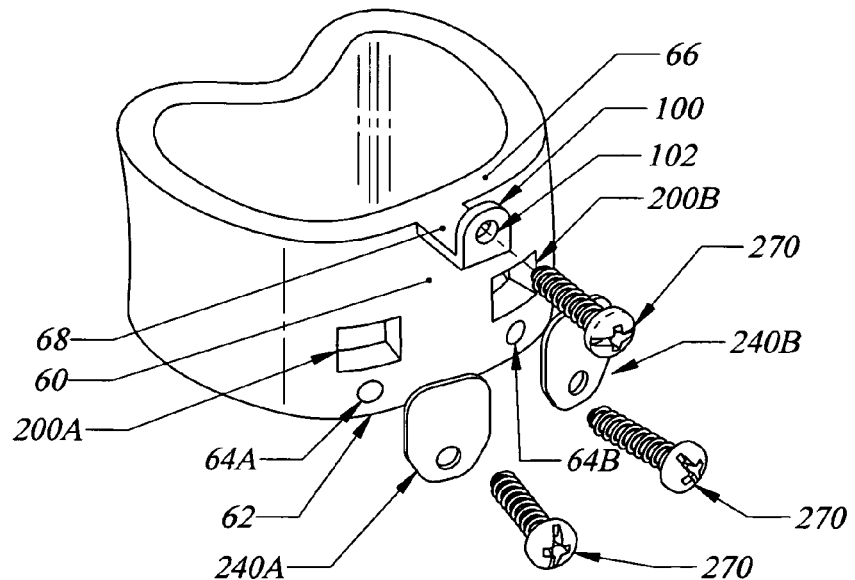
FIG. 8 is an exploded perspective of an anterior curved section of an embodiment of the doughnut-like implant.

FIG. 8 is an exploded perspective of still another embodiment of doughnut-like implant (30). Anterior curved section (60) has lower edge (62), upper edge (66) and arm (68) extending forwardly from anterior curved section (60). Attached to arm (68) is plate (100) that includes aperture (102) for receiving fastener (270). Anterior curved section (60) includes windows (200A and 200B) and apertures (64A and 64B) proximate to windows (200A and 200B). Windows (200A and 200B) allow addition of osteogenic substances into the doughnut-like implant after the implant has been inserted between two vertebras. Along with securing doughnut-like implant (30) to bone, fasteners (270) also secure covers (240A and 240B) about windows (200A and 200B).

Figures 9, 10, 11:
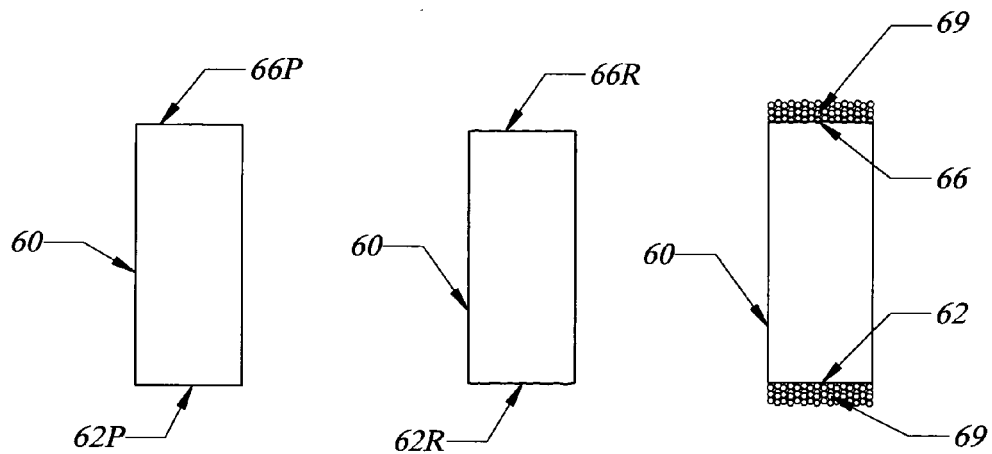
FIG. 9 is a cross-sectional view of an embodiment of anterior curved section of the doughnut-like implant.
FIG. 10 is a cross-sectional view of an embodiment of anterior curved section of the doughnut-like implant.
FIG. 11 is a cross-sectional view of an embodiment of anterior curved section of the doughnut-like implant.

FIG. 9 is a cross-sectional view of an embodiment of anterior curved section (60). In select embodiments, upper edge (66P) is polished and lower edge (62P) is also polished. Although not shown in FIG. 9, upper edge (74) and lower edge (76) of posterior curvature (72) and upper edges (82 and 92) and lower edges (84 and 94) of lateral curvatures (80 and 90) can be polished.

FIG. 10 is a cross-sectional view of an embodiment of anterior curved section (60). In select embodiments, upper edge (66R) is roughened and lower edge (62R) is also roughened. Although not shown in FIG. 10, upper edge (74) and lower edge (76) of posterior curvature (72) and upper edges (82 and 92) and lower edges (84 and 94) of lateral curvatures (80 and 90) can be roughened.

FIG. 11 is a cross-sectional view of an embodiment of anterior curved section (60). In select embodiments, porous coating (69) is attached to upper edge (66) and lower edge (62) of anterior curved section (60). Porous coating (69) can be a biocompatible polymeric layer, ranging from about 1 millimeter to about 2 millimeters in thickness. It is believed that the porous coating enhances bone ingrowth and improves stability of the doughnut-like spinal implant. Although not shown in FIG. 11, upper edge (74) and lower edge (76) of posterior curvature (72) and upper edges (82 and 92) and lower edges (84 and 94) of lateral curvatures (80 and 90) can also be provided with a porous coating to enhance bone ingrowth. Depending on engineering parameters, porous coating (69) can be applied to either polished or roughened edges of the doughnut-like implant.

Figure 12:
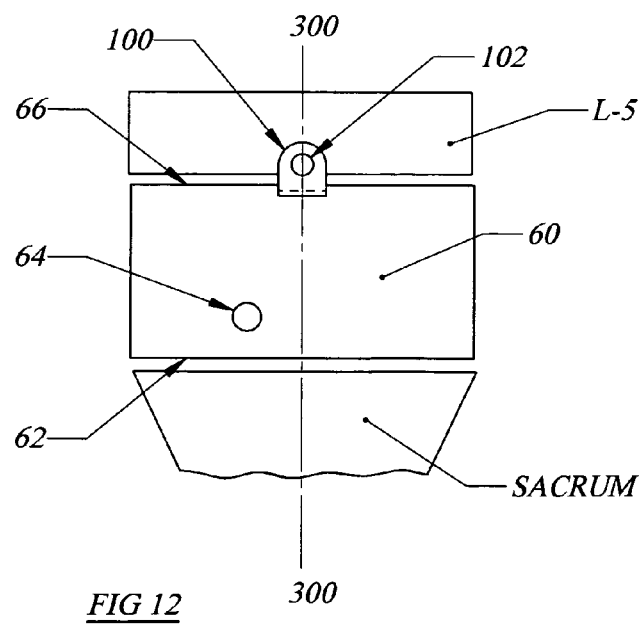
FIG. 12 is a frontal view of an embodiment of the doughnut-like implant.

FIG. 12 is a frontal view of an embodiment doughnut-like implant (30) that is inserted between the lumbar 5 vertebra and the sacrum. A fastener (not shown in this view) can be inserted through aperture (64) of anterior section (60) into the sacrum. As shown in the FIG. 12 embodiment, aperture (64) is offset from centerline (300-300) of anterior section (60). In other embodiments, aperture (64) is not offset from aperture (102). Another fastener (not shown in this view) can be inserted through aperture (102) of plate (100) into the lumbar 5 vertebra.

Figure 13:
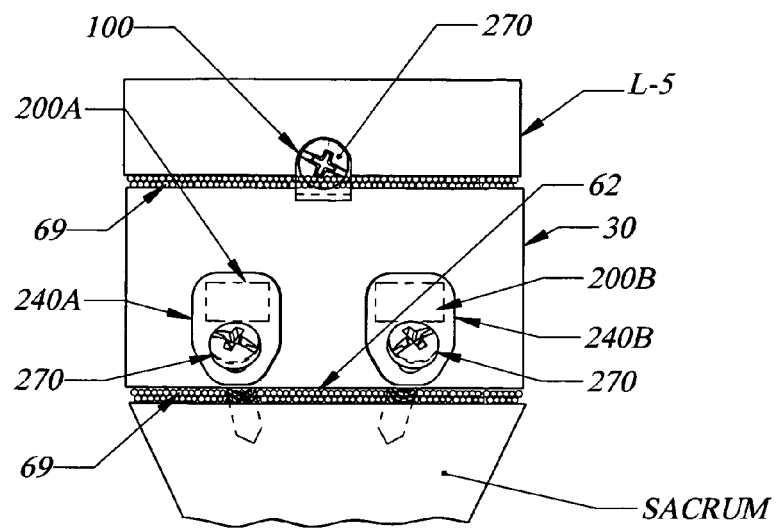
FIG. 13 is a frontal view of an embodiment of the doughnut-like implant.

FIG. 13 is frontal view of an embodiment of doughnut-like implant (30) that is secured between the lumbar 5 vertebra and the sacrum. Upper fastener (270) secures plate (100) to the L-5 vertebra. Porous coating (69) has been applied to upper edge (66) and lower edge (62) of anterior section (30). Window (200A) is covered by cover (240A) and window (200B) is covered by cover (240B). Lower fasteners (270) secure doughnut-like implant (30) to the sacrum and covers (240A and 240B) to the doughnut-like implant.

Figure 14:
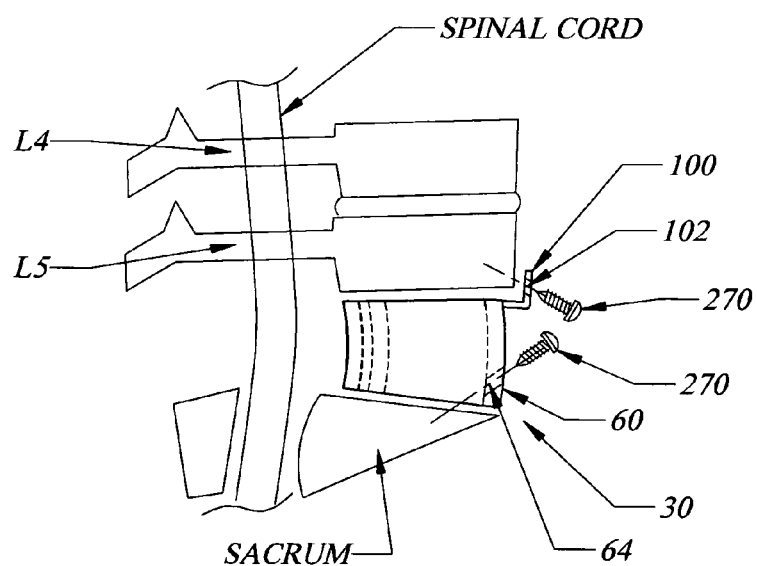
FIG. 14 is a side view of the spinal cord, the sacrum and lumbar 4 and 5 vertebras having an embodiment of the doughnut-like implant inserted between the lumbar 5 vertebra and the sacrum.

FIG. 14 is a side view of the spinal cord, the sacrum and lumbar 4 and 5 vertebras having doughnut-like implant (30) inserted between the lumbar 5 vertebra and the sacrum. Screw (270) is inserted through aperture (102) of plate (100) into the lumbar 5 vertebra. Screw (270) is inserted through aperture (64) of anterior section (60) into the sacrum.

Embodiments of the current doughnut-like implant can have a width of from about 20 millimeters to about 45 millimeters and a depth of from about 10 millimeters to about 30 millimeters. The heights for anterior curvatures of the present invention range from about 3 millimeters to about 25 millimeters and the heights for posterior curvatures of the current invention range from about 3 millimeters to about 15 millimeters.

Having disclosed the invention as required by Title 35 of the United States Code, Applicant now prays respectfully that Letters Patent be granted for his invention in accordance with the scope of the claims appended hereto.

What is claimed is:

1. A biocompatible metallic, plastic or combined metallic-plastic doughnut-like implant capable of frontal insertion between a superior and inferior lumbosacral vertebra; said doughnut-like implant comprising:
   a) an asymmetrical central opening having a central vertical axis;
   b) an anterior curvature protruding forward and away from said central vertical axis, wherein said anterior curvature has superior and inferior edges; said anterior curvature further comprising one or more apertures located proximate said inferior edge for receiving one or more fasteners;
   c) a posterior curvature protruding forward and toward said central vertical axis, wherein said posterior curvature has superior and inferior edges, and wherein said posterior curvature is angled more acutely than said anterior curvature;
   d) a first annular-like side distinct from said anterior and posterior curvatures and connected with said anterior curvature and said posterior curvature, wherein said first annular-like side includes an upper boundary and a lower boundary, and wherein said upper boundary and said lower boundary taper toward each other as said first annular-like side traverses from said anterior curvature to said posterior curvature;
   e) a second annular-like side distinct from said anterior and posterior curvatures and connected with said anterior curvature and said posterior curvature, wherein said second annular-like side includes an upper boundary and a lower boundary, and wherein said upper boundary and said lower boundary taper toward each other as said second annular-like side traverses from said anterior curvature to said posterior curvature;
   f) a forwardly extending arm attached to said superior edge of said anterior curvature; and
   g) a plate comprising an aperture, wherein said plate is connected with said forwardly extending arm, wherein said plate extends upward from said forwardly extending arm, wherein said plate is generally parallel a reference plane intersecting said first annular-like side and said second annular-like side, and wherein said central vertical axis is coplanar with said referenced plane.

2. The invention of claim 1 further comprising one or more windows through said anterior curvature.

3. The invention of claim 2, wherein said apertures located proximate said inferior edge are offset from a vertical centerline of said anterior curvature.

4. The invention of claim 3 further comprising one or more detachable covers for said windows.

5. The invention of claim 4 further comprising a porous coating applied to superior and inferior edges of said anterior and posterior curvatures and said upper and lower boundaries of said first annular-like and said second annular-like sides.

6. A biocompatible metallic, plastic or combined metallic-plastic doughnut-like implant capable of frontal insertion between a superior and inferior lumbosacral vertebra, wherein said doughnut-like implant comprises a plurality of distinct generally upright load supporting curvatures; said doughnut-like implant further comprising:
   a) an asymmetrical central opening, including a central vertical axis, surrounded by said plurality of distinct generally upright load supporting curvatures;
   b) an anterior member, of said plurality of distinct generally upright load supporting curvatures, protruding forward and away from said central vertical axis; said anterior member further comprising one or more apertures proximate an inferior edge of said anterior member;
   c) a posterior member, of said plurality of distinct generally upright load supporting curvatures, protruding forward and toward said central vertical axis; said posterior member angled more acutely than said anterior member;
   d) a first tapered lateral member, of said plurality of distinct generally upright load supporting curvatures, intermediate between and connected with said anterior and said posterior members; said first tapered lateral member comprising an upper boundary and a lower boundary that taper toward each other as said first tapered lateral member traverses from said anterior member to said posterior member;

e) a second tapered lateral member, of said plurality of distinct generally upright load supporting curvatures, intermediate between and connected with said anterior and said posterior members; said second tapered lateral member comprising an upper boundary and a lower boundary that taper toward each other as said second tapered later member traverses from said anterior member to said posterior member;

f) a forwardly extending arm attached proximate an upper edge of said anterior member; and g) a plate, comprising an aperture, connected with said forwardly extending arm, wherein said plate extends upward from said forwardly extending arm.

7. The invention of claim 2, wherein said plate is generally parallel a reference plane intersecting said first tapered lateral member and said second tapered lateral member, wherein said central vertical axis is coplanar with said reference plane.

8. The invention of claim 2, wherein said anterior member further comprises one or more windows.

9. The invention of claim 8 further comprising a porous coating applied to upper and lower edges of said anterior member, said posterior member and said upper and lower boundaries of said tapered lateral members.

10. The invention of claim 9 further comprising one or more detachable covers for said windows, wherein said detachable covers follow a curvature of said anterior member.

11. The invention of claim 10, wherein said apertures located proximate said inferior edge are offset from a vertical centerline of said anterior member.

12. A biocompatible doughnut-like implant capable of frontal insertion between a superior and an inferior vertebra; said doughnut-like implant comprising:

a) an asymmetrical opening comprising a reference generally vertical axis;

b) distinct load bearing curvatures surrounding said asymmetrical opening; said distinct load bearing curvatures comprising superior and inferior edges;

c) a porous coating applied to one or more of said superior or inferior edges;

d) a first load bearing curvature, of said load bearing curvatures, protruding forward and away from said reference axis; said first load bearing curvature further comprising one or more apertures proximate an inferior edge of said first load bearing curvature;

e) a second load bearing curvature, of said load bearing curvatures, protruding toward said reference axis, wherein said second load bearing curvature is angled more acutely than said first load bearing curvature;

f) third and fourth load bearing curvatures, intermediate between and connected with said first load bearing curvature and said second load bearing curvature; and g) a reference plane bisecting said third and fourth load bearing curvatures.

13. The invention of claim 12 further comprising:

a) an arm attached proximate an upper edge of said first load bearing curvature and extending forward from said first load bearing curvature; and b) a plate, generally parallel said reference plane, attached to said arm and extending upward from said arm; and c) an aperture for said plate.

14. The invention of claim 13, wherein said first load bearing curvature further comprises one or more windows.

15. The invention of claim 14, wherein:

a) superior and inferior edges of said third load bearing curvature taper toward each other as said third load bearing curvature traverses from said first load bearing curvature toward said second load bearing curvature; and b) superior and inferior edges of said fourth load bearing curvature taper toward each other as said fourth load bearing curvature traverses from said first load bearing curvature toward said second load bearing curvature.

16. The invention of claim 15 further comprising one or more detachable covers for said windows, wherein each of said detachable covers follows a curvature of its corresponding window.

17. The invention of claim 16, wherein said third and said fourth load bearing curvatures protrude outwardly from said reference axis.

18. The invention of claim 17, wherein said windows and said apertures are offset from a vertical centerline of said first load bearing curvature.

19. A biocompatible doughnut-like implant capable of frontal insertion between a superior and an inferior vertebra; said doughnut-like implant comprising an opening enclosed by a series of interconnected load bearing generally upright sections, wherein adjacent sections forming said opening of said interconnected load bearing generally upright sections include distinct curvatures, and wherein said series further comprises:

a) an anterior section protruding forwardly and comprising one or more apertures proximate an inferior edge of said anterior section;

b) a posterior section protruding forwardly and angled more acutely than said anterior section;

c) first and second opposed lateral sections intermediate between and connected with said forward and said rearward sections; and d) a reference plane bisecting said first and said second opposed lateral sections.

20. The invention of claim 19, wherein:

a) said posterior section comprises a protrusion angle of more than 30 degrees; and b) said anterior section comprises a protrusion angle of less than 30 degrees.

21. The invention of claim 20 further comprising:

a) an arm attached proximate an upper edge of said anterior section and extending forward from said anterior section; and b) a plate, generally parallel said reference plane, attached to said arm and extending upward from said arm; and c) an aperture for said plate.

22. The invention of claim 21, wherein superior and inferior edges of said sections of said series are roughened.

23. The invention of claim 22 further comprising a porous coating applied to a superior edge or an inferior edge or both of one or more of said sections of said series.

24. The invention of claim 23 further comprising one or more windows.

25. The invention of claim 24, wherein said first and said second lateral sections are tapered and protrude outwardly.

26. The invention of claim 25 further comprising one or more detachable covers for said windows, wherein each of said detachable covers follows a curvature of its corresponding window.

27. The invention of claim 26, wherein:

a) upper and lower edges of said first lateral section taper toward each other as said first lateral section traverses from said anterior section toward said posterior section; and b) upper and lower edges of said second lateral section taper toward each other as said second lateral section traverses from said anterior section toward said posterior section.

* * * * *